Figure 1:
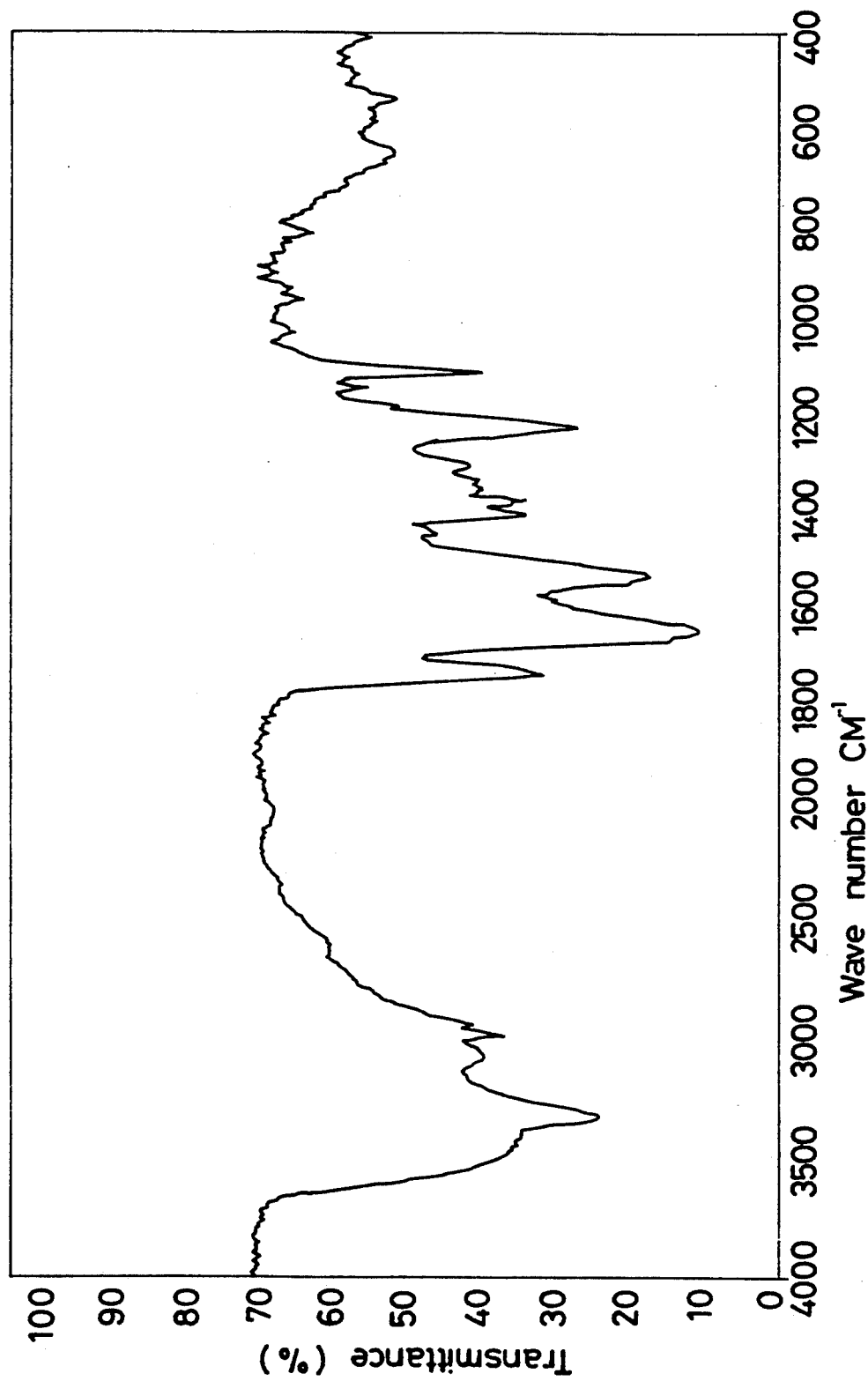

United States Patent [19]

Ogata et al.

[11] Patent Number: 5,223,488
[45] Date of Patent: Jun. 29, 1993

[54] OXIDIZED-TYPE GLUTATHIONE ALKYL ESTER

[75] Inventors: Kazumi Ogata, Toyonaka; Takahiro Sakaue, Itami; Yuichi Isowaki, Settsu; Hideki Tsuruoka, Kawanishi, all of Japan

[73] Assignee: Senju Pharmaceutical Company, Ltd., Osaka, Japan

[21] Appl. No.: 813,722

[22] Filed: Dec. 27, 1991

[30] Foreign Application Priority Data

Dec. 28, 1990 [JP] Japan ................... 2-416855

[51] Int. Cl.$^5$ ...................... A61K 37/00; A61K 37/02
[52] U.S. Cl. ..................... 514/18; 530/331; 530/332; 530/345
[58] Field of Search ............ 530/331, 345, 332; 514/18

[56] References Cited

FOREIGN PATENT DOCUMENTS 6426516 7/1987 Japan .

OTHER PUBLICATIONS

CA 110: 121380x (1989).
JP Abstract vol. 13 No. 208 (May 16, 1989) of JP 64-26516 (Akira Otsu et al.).
Japanese Unexamined Patent Publication No. 15870/1986 (61-15870).

Primary Examiner—Merrell C. Cashion, Jr.
Assistant Examiner—Bennett M. Celsa
Attorney, Agent, or Firm—Millen, White, Zelano and Branigan

[57] ABSTRACT

Presented are an oxidized-type glutathione alkyl ester represented by the formula (I).

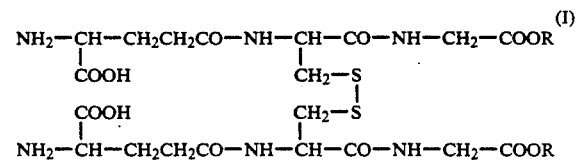

wherein R denotes a lower alkyl group, and a salt thereof: a method of preparing said ester which is comprised of oxidizing a reduced-type glutathione monoalkyl ester represented by the formula (II),

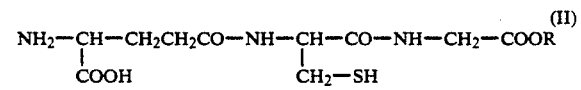

wherein R is as defined above, with the air, hydrogen peroxide or iodine in an aqueous solution: and a pharmaceutical composition and method for suppression of hepatic disorders characterized in that it contains as an active constituent said ester or a pharmaceutically acceptable salt thereof.

7 Claims, 1 Drawing Sheet

OXIDIZED-TYPE GLUTATHIONE ALKYL ESTER

BACKGROUND OF THE INVENTION

The present invention relates to a novel oxidized-type glutathione derivative, more specifically to an oxidized-type glutathione alkyl ester and a pharmaceutically acceptable salt thereof, a method of preparation thereof as well as a pharmaceutical composition containing one of them as an active constituent for suppression of disorders in the liver.

It is known that glutathione alkyl esters (reduced-type) are superior to glutathione in transferability into living bodies, for example to the liver and the kidney, and that they undergo hydrolysis to form glutathione after transferred.

Glutathione monoesters (reduced type) have been described in Japanese Unexamined Patent Publication No. 15870/1986, whereas no description has been given about an oxidized-type glutathione alkyl ester, a method of preparation thereof or a use thereof.

SUMMARY OF THE INVENTION

The inventors have made a study to find a glutathione derivative which has a satisfactory absorbability to tissues as well as a sufficient stability. As a result, the inventors have found that oxidized-type glutathione alkyl esters with an excellent stability are obtained by oxidation of glutathione monoalkyl esters by a simple method i.e., oxidation with the air, hydrogen peroxide or iodine and that these compounds have an excellent pharmaceutical activity. And the studies have been further accumulated to finally accomplish the present invention.

DETAILED DISCUSSION

Therefore, the present invention relates to an oxidized-type glutathione alkyl ester represented by the formula (I) below,

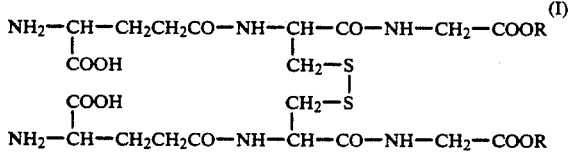

Therein R denotes a lower alkyl group, or a pharmaceutically acceptable salt thereof, a method of preparation thereof and a pharmaceutical composition containing them for suppression of disorders in the liver.

In the present invention, a lower alkyl group is preferably an alkyl group of 1 to 10 carbon atoms. Any of straight, branched or cyclic alkyl groups may be preferably selected as said alkyl groups, and an alkyl group composed of their combination may be preferably used likewise.

Examples of the particularly preferred lower alkyl groups include, methyl, ethyl, n-propyl, isopropyl, cyclopropyl, n-butyl, t-butyl, sec-butyl, n-pentyl, 1-ethylpropyl, isopentyl, benzyl and the like.

The method of preparing the compound of the present invention is as follows.

First, in alcohol and under the presence of an acid, glutathione is converted into an acidic salt of a glutathione monoester represented by the formula (II),

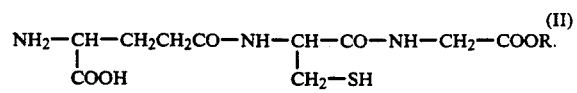

This is then neutralized with an alkali, and to the thus obtained neutral aqueous solution, the air is introduced or hydrogen peroxide or iodine in alcohol is added dropwise while stirring so as to oxidize the glutathione monoester. Herein, the acidic salt of the glutathione monoester may be, for example, a hydrochloride, sulfate or p-toluenesulfonate, although the scope of it is not restricted by these. Above reactions may be easily attained by simple procedures, and the reaction mixture solution thus obtained may then be chromatographed for purification or recrystallized to give the aimed compound.

The compound of the present invention has an activity to suppress the elevation of the levels of GOT, GPT, etc. and efficiently restrains the onset of acute or chronic hepatic disorders. Thus, it may be used for the prophylaxis against and treatment of acute or chronic hepatitis. Moreover, it may also be used advantageously in other disorders in the liver induced by drugs such as acetaminophen. In addition, it is also expected that it may be used for the prevention of the progress and the treatment of cataract.

The compound of the present invention may be appropriately used through an oral or parenteral route. The pharmaceutical composition may be prepared in the form of, for example, tablets, granules, powder or capsules, a liquid preparation such as an injection or eye-drops, or any other form by a known method according to the type and the site of the disorder.

For these preparations, ingredients usually incorporated may suitably be used, which include binders, disintegrators, thickeners, dispersing agents, resorption accelerators, flavoring agents, buffering agents, surfactants, solubilizers, preservatives, emulsifiers, isotonizers, stabilizers and pH adjusting agents.

A suitable dose of the active constituent in general may be, for example, in the range of approximately 1–1000 mg/day for an adult human in the case of injection, and in the range of approximately 10–2000 mg/dosage with several administrations/day for an adult human in the case of oral administration, although it may vary in accordance with the type and severity of the disorder, the age and body weight of the patient, the specific form of the preparation and the like.

The pharmaceutical composition for suppression of hepatic disorders containing as an active constituent the compound of the present invention may contain one of the compounds of the present invention or two or more of them in proper combination, and may also contain other proper constituents having the same or different pharmaceutical activities insofar as they will not hinder the purpose of the present invention.

EXAMPLES

The present invention will be illustrated by the examples below.

EXAMPLE 1
γ-L-GLUTAMYL-L-CYSTEINYLGLYCINE ISOPROPYL ESTER DISULFIDE (OXIDIZED-TYPE GLUTATHIONE ISOPROPYL ESTER)

Method 10 g of γ-L-glutamyl-L-cysteinylglycine isopropyl ester sulfate (GSH isopropyl ester sulfate) is suspended in 200 ml of water. The suspension is then neutralized by a gradual addition of 3.0 g of calcium carbonate. Thus, GSH isopropyl ester is freed and dissolved, while calcium sulfate precipitates. The mixture is then filtered, and to the filtrate is added dropwise 14 ml of 5% hydrogen peroxide while cooling. After stirring for 3 hours, the reaction mixture is concentrated in vacuo at a temperature not higher than 40 °C. To the concentrate is added acetonitrile, and the precipitated crystals are collected by filtration to give 6 g of crude crystals.

The crude crystals are purified by column chromatography (column: YMC ODS 120A S-50, eluant; acetonitrile/water = ¼), and the solvent is evaporated in vacuo from the obtained fraction. The residue is crystallized by an addition of acetonitrile, and recrystallized from water-acetonitrile to give 2.5 g of colorless amorphous crystals.

TLC (silica gel): Rf=0.26 (n-butanol/acetic acid/water=4/1/1).

$[\alpha]^{20}_D = -82.7°$ (c=1, H$_2$O).

Elemental analysis: For $C_{26}H_{44}O_{12}N_6S_2 \cdot 2H_2O$ Calculated(%): C; 42.6, H; 6.60, N; 11.47. Found (%): C; 42.84, H; 6.50, N; 11.52.

FIG. 1 Describes their Spectrum of this compound.

Method B

A solution of GSH isopropyl ester is obtained 15 analogously to Method A using 10 g of GSH isopropyl ester sulfate. To this is added dropwise a 2 w/v % iodine solution in methanol at room temperature until the reacting mixture solution turns pale yellow. The mixture is stirred for further 2 hours at 40° C. and then neutralized with calcium carbonate. The precipitated inorganic crystals are removed by filtration, and the filtrate is concentrated in vacuo. To the concentrate is added acetonitrile, and the precipitated crystals are collected by filtration to give 5 g of crude crystals. Then the crystals are purified by column chromatography analogously to Method A to give 1.9 g of the purified product.

Method

A solution of GSH isopropyl ester obtained analogously to Method A using 10 g of GSH isopropyl ester sulfate is vigorously stirred for 24 hours at room temperature while introducing the air. The mixture is then treated analogously to Method A to give 2.3 g of purified product.

EXAMPLE 2
γ-L-GLUTAMYL-L-CYSTEINYLGLYCINE ETHYL ESTER DISULFIDE (OXIDIZED-TYPE GLUTATHIONE ETHYL ESTER)

Analogously to Method A in Example 1, 10 g of γ-L-glutamyl-L-cysteinylglycine ethyl ester hydrochloride and 3.0 g of calcium carbonate are used, and oxidation is performed with 5% hydrogen peroxide. Analogous combination of a column (YMC DDS 120A S-50) and an eluant (acetonitrile/water=7/43) are used for separation. The crystals obtained are recrystallized from water-acetonitrile to give 1.5 g of colorless amorphous crystals.

TLC (silica gel): Rf=0.16 (n-butanol/acetic acid/water=4/1/1).

$[\alpha]^{20}_D = -89.7°$ (c=1, H$_2$O).

Elemental analysis: For $C_{24}H_{40}O_{12}N_6S_2 \cdot 2H_2O$ Calculated (%): C; 40.90, H; 6.2g, N; 11.92. Found (%): C; 40.62. H; 6.41, N; 11.62.

Pharmacological Test

Method

Male Wistar rats with a body weight of about 180 g were fasted for 24 hours and orally administered, through a cannula for oral administration, 87-349 mg of oxidized-type glutathione isopropyl ester (hereinafter also referred to as "GSSG isopropyl"), which is one of the compounds of the present invention, 102 mg of reduced-type glutathione isopropyl ester ½ H$_2$SO$_4$.½ H$_2$O (87 mg as reduced type glutathione isopropyl ester (hereinafter also referred to as "GSH isopropyl")) or 5% gum arabic solution as a control, respectively. 1 hour later, 400 mg/kg of acetaminophen, a compound which may induce disorders in the liver, was intra peritoneally administered. 24 hours later, the rats were anesthetized with pentobarbital and the blood was collected from the abdominal aorta, and s-GOT and s-GPT were measured to compare the hepatic disorder suppressing effect of GSSG isopropyl with that of GSH isopropyl.

Result

As a result, It was demonstrated that the elevation of s-GOT and s-GPT is significantly suppressed dose-dependently by the administration of 87-349 mg/kg of GSSG isopropyl as shown in Table 1. It was also demonstrated that the administration of 102 mg/kg of GSH isopropyl sulfate significantly suppresses the elevation of s-GOT and s-GPT, and that the administration of 87 mg/kg of GSSG isopropyl exhibits a hepatic disorder suppressing effect which is almost equivalent to that exhibited by the administration of 102 mg/kg of GSH isopropyl sulfate.

TABLE 1
Suppressive effect of GSSG isopropyl and GSH isopropyl on acetaminophen-induced liver disorder in the rat.

| Test compound | Dose (mg/kg) | s-GOT (IU/l) | s-GPT (IU/l) |
| --- | --- | --- | --- |
| 5% gum arabic | — | 8632 ± 2397 | 4505 ± 1283 |
| GSSG isopropyl | 87[0.125] | 430 ± 236*[1] (95.0) | 231 ± 152*[1] (94.9) |
| GSSG isopropyl | 174[0.25] | 352 ± 104*[1] (95.9) | 154 ± 46*[1] (96.6) |
| GSSG isopropyl | 349[0.5] | 119 ± 11*[2] (98.6) | 39 ± 3*[1] (99.1) |
| GSH isopropyl Sulfate | 102[0.25] | 475 ± 156*[1] (94.5) | 253 ± 97*[1] (94.4) |

In the Table, each value represents the mean ± S. E. (n=4-8). The figure in [] is the molar expression (mmol/kg) of the dose of the tested compound. The figure in () represents inhibition rate.

Significant difference from 5% gum arabic solution: *1; p<0.05, *2; p<0.01

| Composition example 1 | Oral tablets |
|---|---|
| oxidized-type glutathione isopropyl ester | 100 mg |
| lactose | 80 mg |
| starch | 17 mg |
| magnesium stearate | 3 mg |

The above ingredients are formed into tablet by a conventional method. Sugar coating may optionally be made.

| Composition example 2 | Injection |
|---|---|
| oxidized type glutathione isopropyl ester | 1.0 g |
| sodium chloride | 0.7 g |
| distilled water for injection | 100 ml |

The above ingredients are admixed and sterilized by filtration. 2 ml each of the filtrate is aseptically filled in a glass vial, and the vial then is sealed by heat to form an injection.

| Composition example 3 | Eye drops |
|---|---|
| oxidized type glutathione isopropyl ester | 1.0 g |
| boric acid | 0.7 g |
| sodium chloride | 0.5 g |
| methyl p-hydroxybenzoate | 0.02 g |
| chlorobutanol | 0.3 g |
| 10 w/v % sodium hydroxide solution | q.s. (to pH 6.0) |
| sterile purified water | to 100 ml |

The above ingredients are admixed to dissolve by a conventional method. The solution is then sterilized by filtration and filled in sterile containers for eye-drops.

What is claimed is:

1. An oxidized glutathione alkyl ester represented by the formula (I),

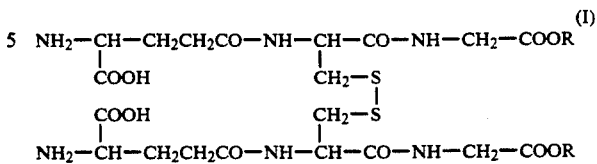

wherein R denotes a lower alkyl group, or a pharmaceutically acceptable salt thereof.

2. A pharmaceutical composition comprising in admixtures with a pharmaceutically acceptable carrier an oxidized glutathione alkyl ester represented by the formula (I),

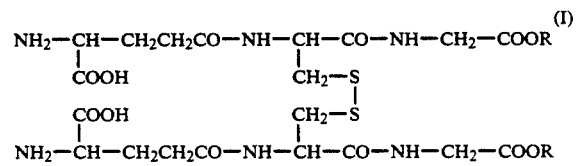

wherein R denotes a lower alkyl group, or a pharmaceutically acceptable salt thereof.

3. The pharmaceutical composition of claim 2 which is in the form of tablets, granules, powder, capsules or injection.

4. The compound of claim 1 wherein R is isopropyl.

5. The compound of claim 1 wherein R is ethyl.

6. The pharmaceutical composition of claim 1 wherein R of Formula (I) is isopropyl.

7. The pharmaceutical composition of claim 1 wherein R of Formula (I) is ethyl.

* * * * *